United States Patent
Lundberg (10) Patent No.: US 8,480,583 B2
(45) Date of Patent: Jul. 9, 2013

(54) METHODS AND APPARATUS FOR 4D DATA ACQUISITION AND ANALYSIS IN AN ULTRASOUND PROTOCOL EXAMINATION

(75) Inventor: Vidar Lundberg, Trondheim (NO)

(73) Assignee: General Electric Company, Schenectady, NY (US)

( * ) Notice: Subject to any disclaimer, the term of this patent is extended or adjusted under 35 U.S.C. 154(b) by 1426 days.

(21) Appl. No.: 11/873,182

(22) Filed: Oct. 16, 2007

(65) Prior Publication Data

US 2009/0099449 A1    Apr. 16, 2009

(51) Int. Cl.
*A61B 8/00*    (2006.01)

(52) U.S. Cl.
USPC ........... 600/437; 600/443; 600/447; 600/438; 600/453; 600/407

(58) Field of Classification Search
USPC ... 600/437, 443, 447, 438, 453–456; 382/128
See application file for complete search history.

(56) References Cited

U.S. PATENT DOCUMENTS

| | | | |
|---|---|---|---|
| 5,546,807 A | 8/1996 | Oxaal et al. | |
| 5,986,662 A | 11/1999 | Argiro et al. | |
| 6,213,944 B1 | 4/2001 | Miller et al. | |
| 6,241,675 B1 | 6/2001 | Smith et al. | |
| 6,276,211 B1 | 8/2001 | Smith | |
| 6,354,997 B1 | 3/2002 | Holley et al. | |
| 6,409,669 B1 | 6/2002 | Hager et al. | |
| 6,488,629 B1 | 12/2002 | Saetre et al. | |
| 6,500,123 B1 | 12/2002 | Holloway et al. | |
| 6,503,203 B1 | 1/2003 | Rafter et al. | |
| 6,676,599 B2 | 1/2004 | Torp et al. | |
| 6,951,543 B2 | 10/2005 | Roundhill | |
| 7,660,623 B2 * | 2/2010 | Hunter et al. | 600/424 |
| 7,697,972 B2 * | 4/2010 | Verard et al. | 600/424 |
| 2002/0072671 A1 | 6/2002 | Chenal et al. | |
| 2003/0055308 A1 | 3/2003 | Friemel et al. | |
| 2005/0049500 A1 * | 3/2005 | Babu et al. | 600/443 |
| 2005/0281444 A1 | 12/2005 | Lundberg et al. | |
| 2006/0239540 A1 * | 10/2006 | Serra et al. | 382/154 |
| 2007/0127789 A1 * | 6/2007 | Hoppel et al. | 382/128 |

FOREIGN PATENT DOCUMENTS

| | | |
|---|---|---|
| EP | 1 167 996 A | 1/2002 |
| EP | 1 416 443 A | 5/2004 |

OTHER PUBLICATIONS

Sugeng et al., Biplane Stress Echocardiography Using a Prototype Matrix-array Transducer, Copyright 2003 by the American Society of Echocardiography, 0894-7317/2003/$30.00 + 0, doi: 10.1016/S0894-7317(03)00469-3, pp. 937-941.

* cited by examiner

*Primary Examiner* — Unsu Jung
*Assistant Examiner* — Joel Lamprecht
(74) *Attorney, Agent, or Firm* — The Small Patent Law Group; Dean D. Small (57) ABSTRACT

Methods and apparatus for 4D data acquisition and analysis in an ultrasound protocol examination are provided. The method includes acquiring 4D ultrasound scan data during a protocol based examination. The method further includes aligning images formed from the 4D ultrasound scan data while the 4D ultrasound scan data is being acquired to allow the automatic extraction of standard imaging projections.

22 Claims, 7 Drawing Sheets

METHODS AND APPARATUS FOR 4D DATA ACQUISITION AND ANALYSIS IN AN ULTRASOUND PROTOCOL EXAMINATION

BACKGROUND OF THE INVENTION

This invention relates generally to diagnostic imaging systems, and more particularly, to methods and apparatus for 4D image acquisition and analysis in an ultrasound protocol examination.

Ultrasound methods and systems exist for use in image data acquisition and medical diagnostics. These methods and systems can acquire ultrasound data and volume render the three-dimensional (3D) images for display, which is often referred to as ultrasound volume imaging. The 3D images also may be combined in time to produce a moving 3D image, which is often referred to as 4D ultrasound imaging. Thus, 4D ultrasound imaging adds the dimension of time to 3D volume imaging, thereby allowing the visualization of anatomy moving in real-time.

Various features have been proposed to facilitate patient examination and diagnosis based on ultrasound images of a patient. For example, in protocol based medical imaging examinations, such as stress-echo type heart studies, portions of the heart may be scanned before and after a stress test to provide corresponding base-line and stress-level images of the selected portions of the heart. In this type of study the patient's heart rate is increased by applying stress (typically physical or pharmacological stress) to the patient, and thereafter there is a limited time to acquire the necessary imaging projections of the heart.

In 4D imaging, it is possible to acquire over time images of the entire organ under investigation with the information needed for analysis extracted at a later time. In many cases, the images in the protocol have some type of relation. For example, a set of images may be acquired in order to show at different times (e.g., image of a heart under different stress levels at different times) the same projection or orientation relative to the organ under investigation. In such instances, the image acquisition setup should be the same at all stages of the imaging protocol. This consistent setup and acquisition will facilitate later comparison of the images to show changes in the organ under investigation. Moreover, in certain examinations, such as a stress-echo protocol examination, acquisition of different images of the heart should occur over a short time period of time in order to image the heart at the different stress levels.

Thus, in order to properly analyze acquired images, different images acquired over time for a particular protocol must be aligned. In 4D imaging it is particularly important to ensure the same geometric orientation of all acquired volume images over different time periods. Failure to properly align the volume images can result in difficulty in analysis and improper diagnosis. Additionally, in stress-echo examinations, if the imaging is not performed in a short enough time period, lower sensitivity of the examination may result, for example, due to some myocardial segments not being properly evaluated at a peak stress level.

BRIEF DESCRIPTION OF THE INVENTION

In accordance with one embodiment, a method for acquiring four-dimensional (4D) ultrasound images in a protocol based examination is provided. The method includes acquiring 4D ultrasound scan data during a protocol based examination. The method further includes aligning images formed from the 4D ultrasound scan data while the 4D ultrasound scan data is being acquired to allow the automatic extraction of standard imaging projections. A four-dimensional (4D) protocol based examination also may be performed using this method.

In accordance with another embodiment, an ultrasound system is provided that includes a probe configured to acquire ultrasound volume data for a protocol based examination. The ultrasound system further includes a processor configured to process aligned four-dimensional (4D) images formed from the ultrasound volume data while the ultrasound volume data is being acquired to automatically extract standard image projections.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
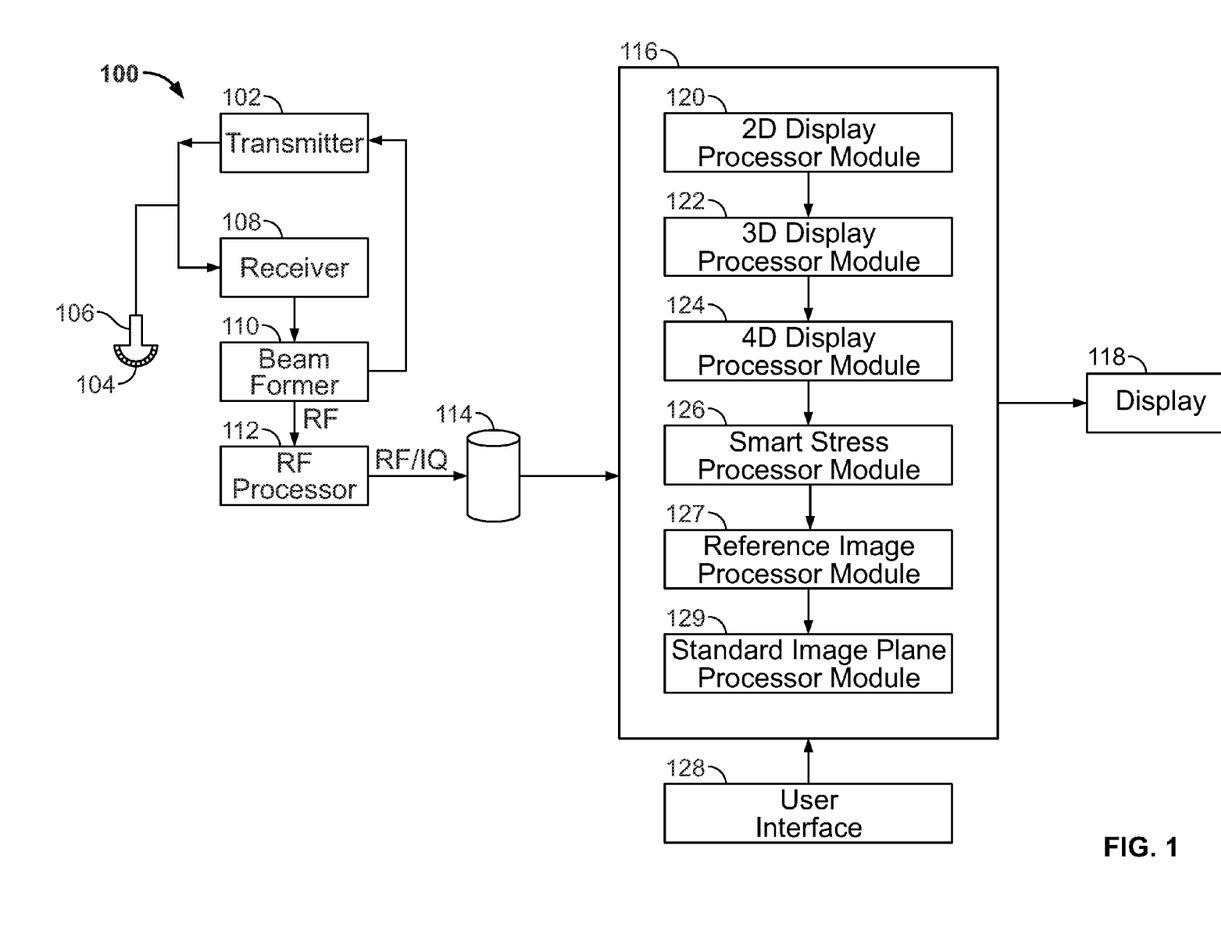
FIG. 1 is a block diagram of an ultrasound system formed in accordance with an embodiment of the invention.

FIG. 1 is a block diagram of an ultrasound system 100 formed in accordance with various embodiments of the invention. The ultrasound system 100 is configured to acquire four-dimensional (4D) ultrasound images for protocol based examinations. For example, 4D images of a human heart may be acquired during different levels of a stress-echo examination. The ultrasound system 100 includes a transmitter 102 that, under the control of a beamformer 110, drives an array of elements 104 (e.g., piezoelectric elements) within a probe 106 to emit pulsed ultrasonic signals into a body. A variety of different probe geometries may be used. The ultrasonic signals are back-scattered from structures in the body, like blood cells or muscular tissue, to produce echoes that return to the elements 104. The echoes are received by a receiver 108. Accordingly, in operation, the probe 106 transmits an ultrasound signal and receives the echoes.

The probe 106 may simultaneously transmit and receive multiple beams for obtaining ultrasound data. The use of simultaneous transmitted beams is known as Multi Line Transmit (MLT). The required separation between the simultaneously transmitted beams is maintained either spatially or through the use of codes. The use of codes for the separation is called Coded Excitation as is known. Each transmit beam uses a coded transmit pulse that the receiver can use to separate the signals. In accordance with other embodiments of the invention, collected input data is received using Multi Line Acquisition (MLA) as is known (e.g., 16 MLA with IQ-interpolation).

The received echoes are provided to the beamformer 110, which performs beamforming and outputs an RF signal. The RF signal then is provided to an RF processor 112. Alternatively, the RF processor 112 may include a complex demodulator (not shown) that demodulates the RF signal to form IQ data pairs representative of the echo signals. The RF or IQ signal data may then be stored in a memory 114.

It should be noted that the ultrasound system 100 may be configured to operate with different types of probes and acquire data at different rates. For example, in various embodiments, ultrasound data is acquired at a rate of at least twenty-five frames per second. Optionally, ultrasound data is acquired at a rate of at least thirty frames per second.

The ultrasound system 100 also includes a processor 116 to process the acquired ultrasound information (e.g., RF signal data or IQ data pairs) and prepare frames of ultrasound information for display on display 118. The processor 116 is adapted to perform on the acquired ultrasound data one or more processing operations according to a plurality of selectable ultrasound modalities or modes of operation. Acquired ultrasound data may be processed and displayed in real-time during a scanning session as the echo signals are received. Additionally or alternatively, the ultrasound data may be stored temporarily in memory 114 during a scanning session and then processed and displayed in an off-line operation.

The processor 116 includes a two-dimensional (2D) display processor module 120 that may process from the memory 114 (which may include an image buffer) one or more sets of frames of ultrasound data having a common orientation to produce one or more 2D images or views of the scanned object. The images then may be displayed in one or more quadrants of the display 118 as described in more detail below. For example, the images frames processed by the 2D display processor module 120 may produce different 2D views of an imaged heart (e.g., 4-chamber view, apical 2-chamber view, and an apical long-axis (APLAX) view). The various views, for example, of the human heart may be displayed in different quadrants of the display 118. For example, real-time scanning and display of a 2D plane in real time may be provided. As another example, several scanned 2D cineloops also may be replayed simultaneously on the display 118. As still further example, a number of previously scanned cineloops also may be displayed together with a live 2D image, synchronized by live ECG.

The processor 116 also may include a 3D display processor 122 to process frames of stored ultrasound data or the outputs from the 2D display processor module 120. The 3D display processor module 122 may combine, for example, three views to form a tri-plane view in one quadrant of the display 118. The tri-plane view may show a 3D image, for example, a 3D image of the human heart, aligned with respect to the three intersecting planes of the tri-plane. In one embodiment, the three planes of the tri-plane intersect at a common axis of rotation. In other embodiments, any number of planes may have any orientation. For example, in a cardiac application, the user may want to acquire a number of short-axis scan planes simultaneously from the parasternal window at different levels from the apex to mitral plane in the heart. In this case, N number of planes are acquired with the same rotation angle, but different tilt angle.

The processor 116 also may include a 4D display processor module 124 to process frames of stored ultrasound data or the outputs from the 3D display processor module 122. The 4D display processor module 124 may combine, for example, multiple 3D volumes to form multiple moving images that appear on the display 118 in real-time. Thus, multiple different views of, for example, a moving heart may be displayed on the display 118.

The processor 116 also may include additional modules to facilitate the acquisition and/or analysis of 4D images during a protocol based examination. In particular, the processor 116 may include a smart stress processor module 126 that is used to maintain the orientations of different 4D images during different acquired time periods. For example, in a stress-echo examination, the smart stress processor module 126 compares the various 4D images and maintains the same orientation of the different 4D images during different imaged stress levels of the heart as described in more detail below. The processor 116 also may include a reference image processor module 127 that generates reference images for different acquisition portions of a 4D protocol based examination as described in more detail below. The processor 116 additionally may include a standard image plane processor module 129 that automatically extracts standard image projections from each of a plurality of image views as described in more detail below.

The processor 116 is also connected to a user interface 128 that may control operation of the processor 116 as described in more detail below. The user interface 128 may facilitate the acquisition of 4D volume images during a protocol based examination.

The display 118 includes one or more monitors that present patient information, including diagnostic ultrasound images to the user for diagnosis and analysis (e.g., 4D standard apical views of the heart). The memory 114 may store three-dimensional data sets of the ultrasound data, where such 3D data sets are accessed to present 3D and 4D images as described herein. The images may be modified and the display settings of the display 118 also manually adjusted using the user interface 128.

Figure 2:
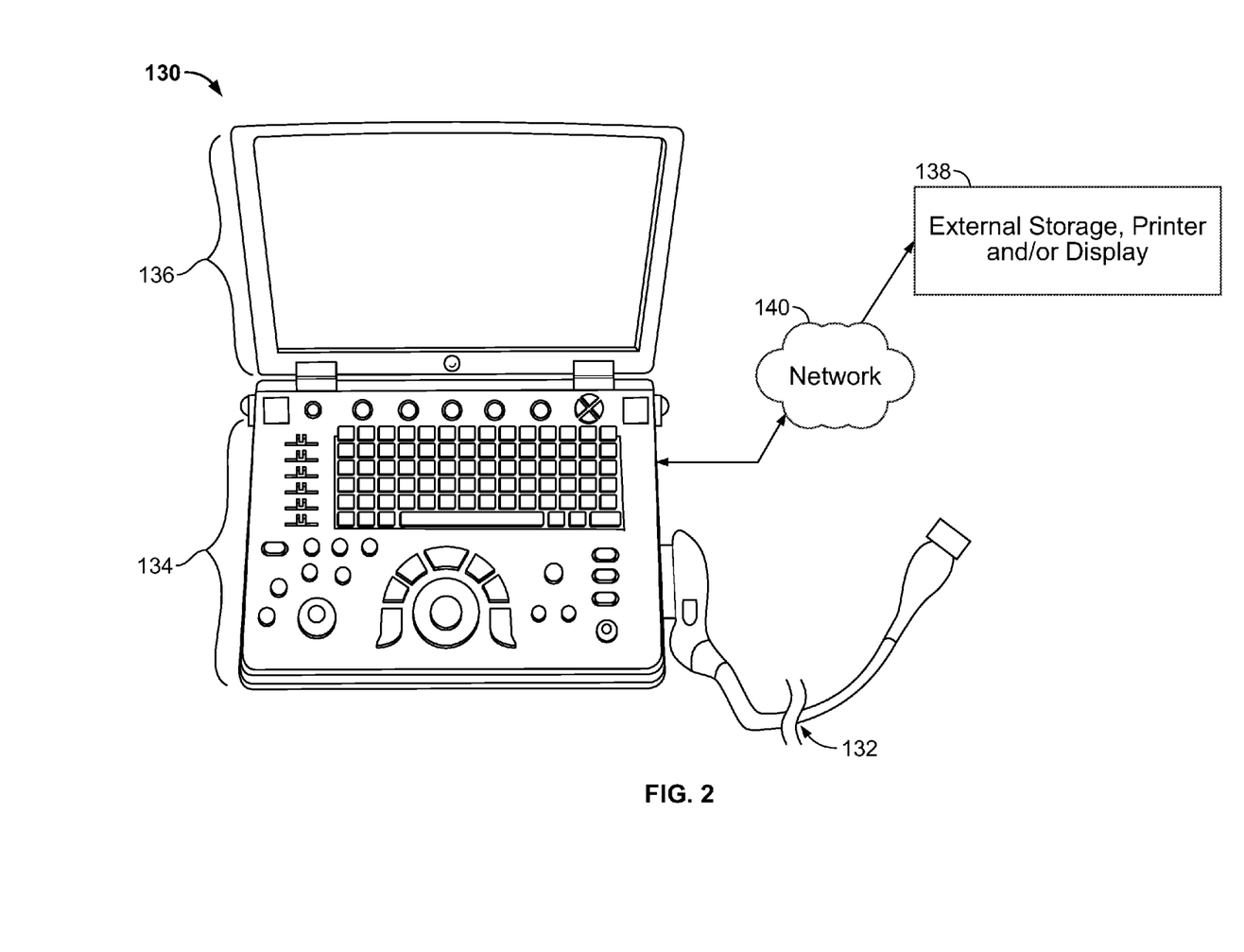
FIG. 2 illustrates a miniaturized ultrasound system formed in accordance with an embodiment of the invention.
Figure 3:
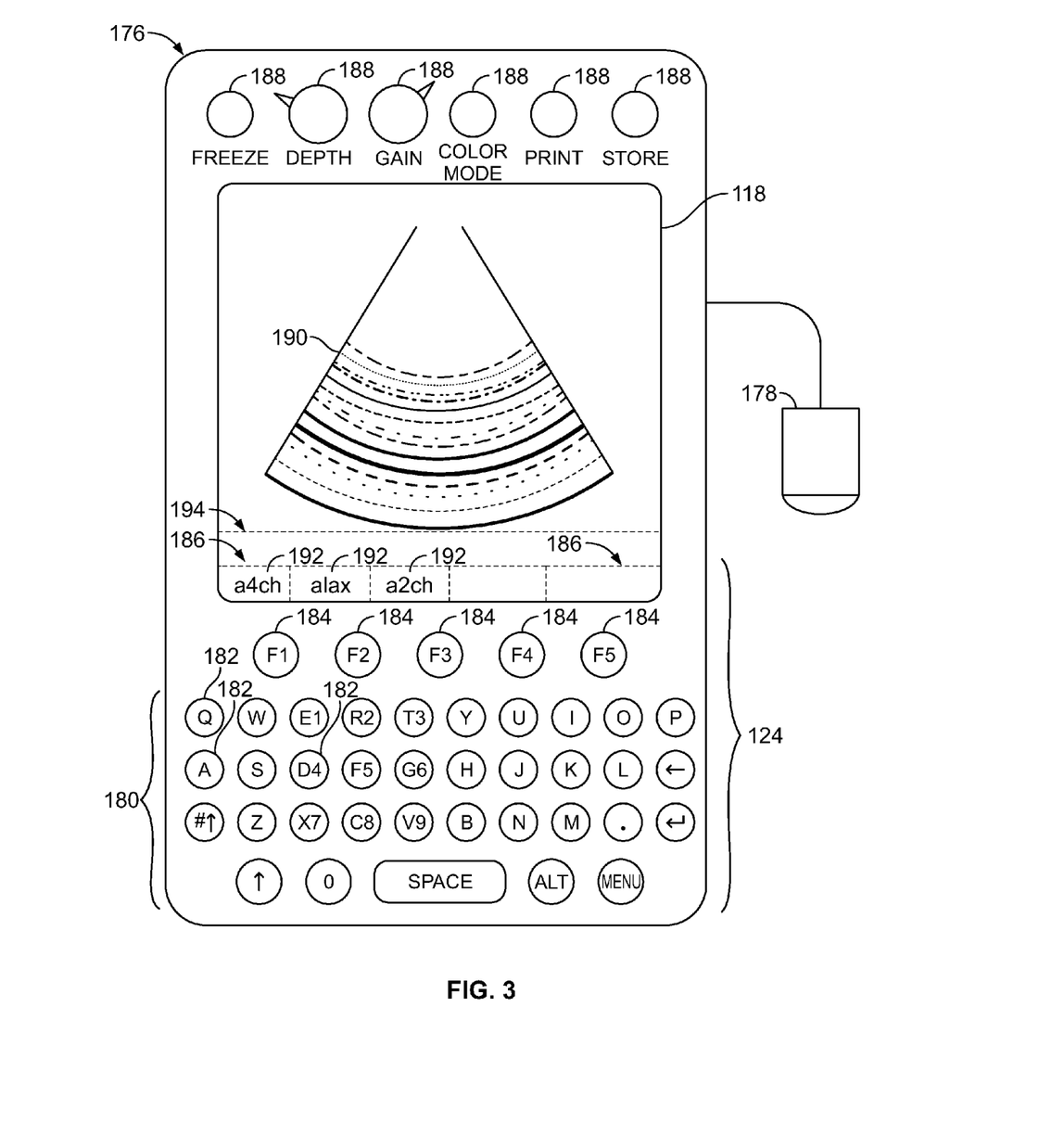
FIG. 3 illustrates a hand carried or pocket-sized ultrasound imaging system formed in accordance with an embodiment of the invention.
Figure 4:
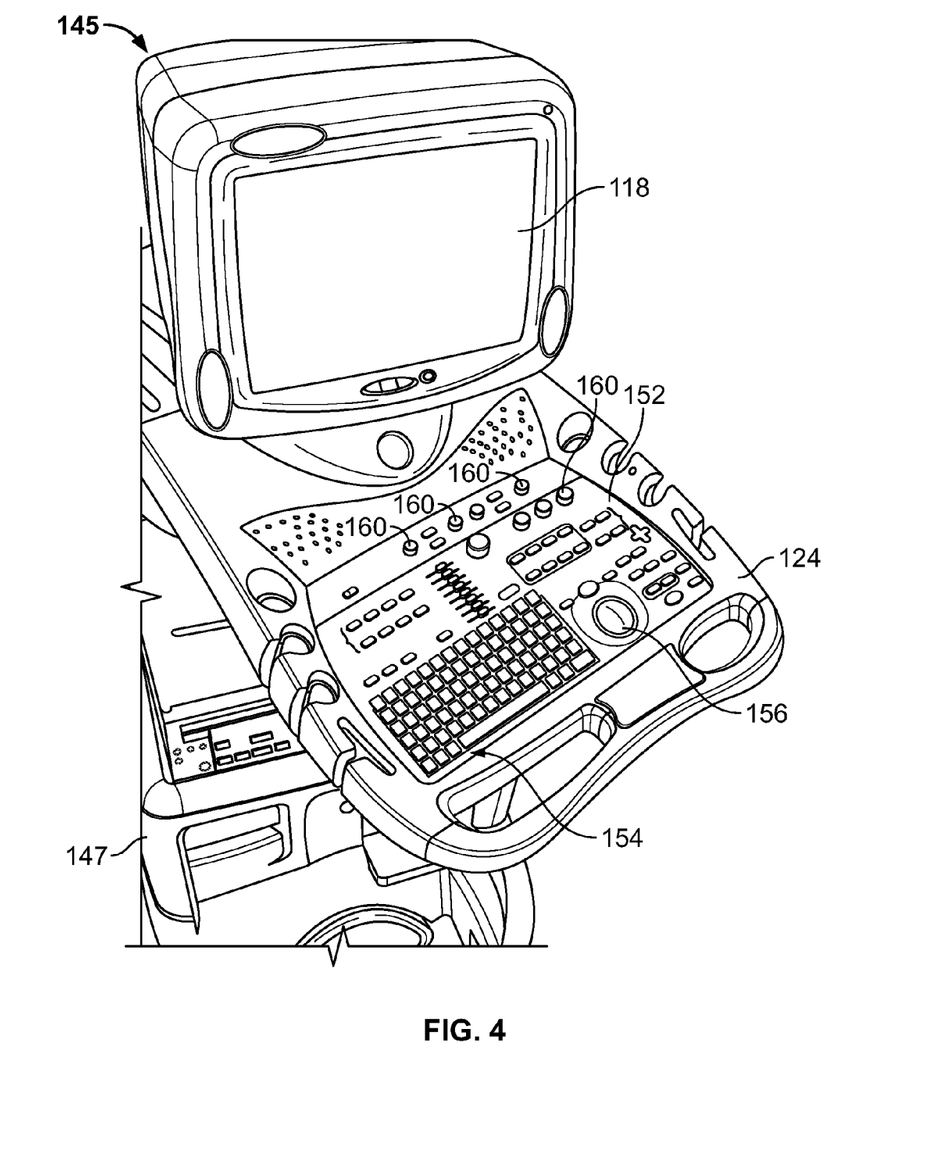
FIG. 4 illustrates a console type ultrasound imaging system formed in accordance with an embodiment of the invention.

The ultrasound system 100 of FIG. 1 may be embodied in a small-sized system, such as laptop computer or pocket-sized system as well as in a larger console type system. FIGS. 2 and 3 illustrate small-sized systems, while FIG. 4 illustrates a larger system.

FIG. 2 illustrates a miniaturized ultrasound system 130 having a probe 132 that may be configured to acquire 3D or 4D ultrasonic data. For example, the probe 132 may have a 2D array of elements 104 as discussed previously with respect to the probe 106 of FIG. 1. A user interface 134 (that may also include an integrated display 136) is provided to receive commands from an operator. As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer. The ultrasound system 130 is easily portable by the operator. The integrated display 136 (e.g., an internal display) is configured to display, for example, one or more 4D medical images during a protocol based examination.

The ultrasonic data may be sent to an external device 138 via a wired or wireless network 140 (or direct connection, for example, via a serial or parallel cable or USB port). In some embodiments, the external device 138 may be a computer or a workstation having a display. Alternatively, the external device 138 may be a separate external display or a printer capable of receiving image data from the hand carried ultrasound system 130 and of displaying or printing images that may have greater resolution than the integrated display 136.

FIG. 3 illustrates a hand carried or pocket-sized ultrasound imaging system 176 wherein the display 118 and user interface 124 form a single unit. By way of example, the pocket-sized ultrasound imaging system 176 may be a pocket-sized or hand-sized ultrasound system approximately 2 inches wide, approximately 4 inches in length, and approximately 0.5 inches in depth and weighs less than 3 ounces. The pocket-sized ultrasound imaging system 176 generally includes the display 118, user interface 124, which may or may not include a keyboard-type interface and an input/output (I/O) port for connection to a scanning device, for example, an ultrasound probe 178. The display 118 may be, for example, a 320×320 pixel color LCD display (on which a medical image 190 may be displayed). A typewriter-like keyboard 180 of buttons 182 may optionally be included in the user interface 124.

Multi-function controls 184 may each be assigned functions in accordance with the mode of system operation (e.g., displaying different views). Therefore, each of the multi-function controls 184 may be configured to provide a plurality of different actions. Label display areas 186 associated with the multi-function controls 184 may be included as necessary on the display 118. The system 176 may also have additional keys and/or controls 188 for special purpose functions, which may include, but are not limited to "freeze," "depth control," "gain control," "color-mode," "print," and "store."

One or more of the label display areas 186 may include labels 192 to indicate the view being displayed or allow a user to select a different view of the imaged object to display. For example, the labels 192 may indicate different views of an imaged heart including a 4-chamber view (a4ch), a long axis view (alax) or a 2-chamber view (a2ch). The selection of different views also may be provided through the associated multi-function control 184. For example, the a4ch view may be selected using the multi-function control F5. The display 118 may also have a textual display area 194 for displaying information relating to the displayed image view (e.g., notes relating to the particular image)

It should be noted that the various embodiments may be implemented in connection with miniaturized or small-sized ultrasound systems having different dimensions, weights, and power consumption. For example, the pocket-sized ultrasound imaging system 176 and the miniaturized ultrasound system 130 of FIG. 2 may provide the same scanning and processing functionality as the system 100 (shown in FIG. 1).

FIG. 4 illustrates a console type ultrasound imaging system 145 provided on a movable base 147. The ultrasound imaging system 145 may also be referred to as a cart-based system. A display 118 and user interface 124 are provided and it should be understood that the display 118 may be separate or separable from the user interface 124. The user interface 124 may optionally be a touchscreen, allowing the operator to select options by touching displayed graphics, icons, and the like.

The user interface 124 also includes control buttons 152 that may be used to control the ultrasound imaging system 145 as desired or needed, and/or as typically provided. The user interface 124 provides multiple interface options that the user may physically manipulate to interact with ultrasound data and other data that may be displayed, as well as to input information and set and change scanning parameters and viewing angles, etc.

Figure 5:
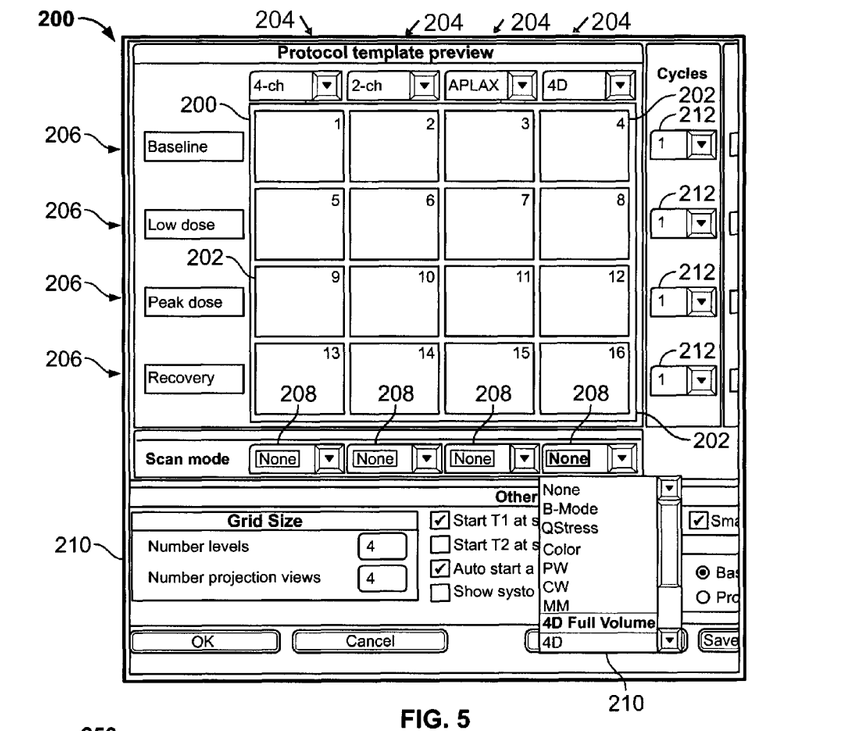
FIG. 5 is a display illustrating a protocol template formed in accordance with an embodiment of the invention.

Various embodiments of the invention provide one or more methods for acquiring 4D ultrasound data during a protocol based examination. In the various embodiments, a protocol template 200 may be provided as shown in FIG. 5. The protocol template 200 defines, among other elements and parameters, the various cut planes, format and position for images to be acquired during an ultrasound scan. In the illustrated protocol template 200, the various cells 202 are configured for use with a stress-echo examination. Each cell 202 corresponds to a particular image view to be acquired at a particular stress level of the stress-echo examination. In the protocol template 200 the columns 204 define the image views (e.g., 4-chamber (4-ch), 2-chamber (2-ch), apical long axis (APLAX) and 4D) and the rows 206 define the different stress levels (e.g., baseline, low dose, peak dose and recovery) for each of the views. A corresponding label may be provided in connection with each column 204 and row 206. Thus, differences in the images produced for baseline and corresponding different stress levels, which may be physically or pharmacologically induced (as illustrated) occur due to the inducement of the different stress levels in the patient.

It should be noted that at least one of the columns 204 is set up to acquire 4D ultrasound datasets with the corresponding scan mode for each view selected using a selectable element 208 (e.g., drop down menu 210). In the illustrated example of FIG. 5, the 4D Full Volume is shown as being selected using a drop down menu 210 of the selectable element 208 for the 4D column 204. It should be noted that different acquisition modes may be selected (e.g., B-mode, Qstress, Color, etc.). Additionally, variations to the acquisition modes may be selected. For example, a real-time full volume 4D acquisition may be selected or a gated 4D acquisition may be selected.

It further should be noted that other parameters or requirements for the stress-echo examination protocol (or other examination protocol) may be selected. For example, the grid size protocol template 200 may be defined by a number of levels and a number of projection views using a Grid Size control portion 210 of the protocol template 200. Additionally, the number of cycles for each stress level may be define using a cycles selectable element 212 (e.g., drop down menu) corresponding to each row 206. Additionally, the protocol template 200 allows, for example, for combining 2D and 4D image recordings (and other modes).

For each cell 202, column 204 (view) or rows 206 (stress level), scan parameters, display parameters or system parameters may be defined, for example, corresponding to gain, frequency and focus depths. Additional parameters within the template elements may be automatically selected based on the values entered for required parameters.

Figure 6:
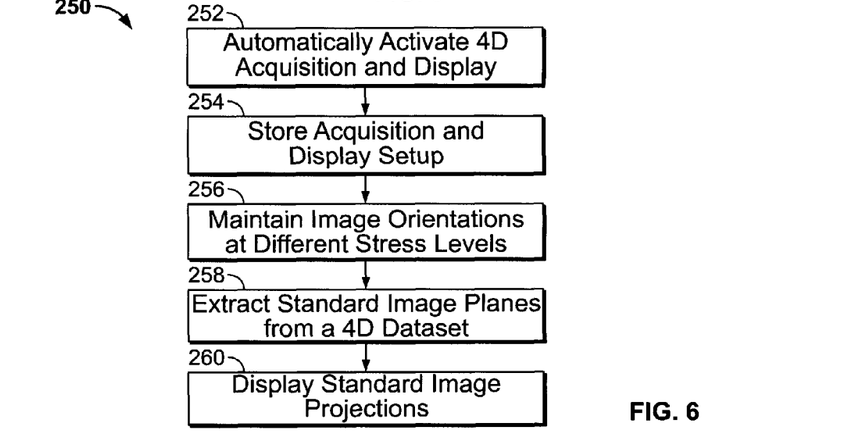
FIG. 6 is a flowchart of a method for performing 4D image acquisition and analysis in a protocol based examination in accordance with an embodiment of the invention.
Figure 7:
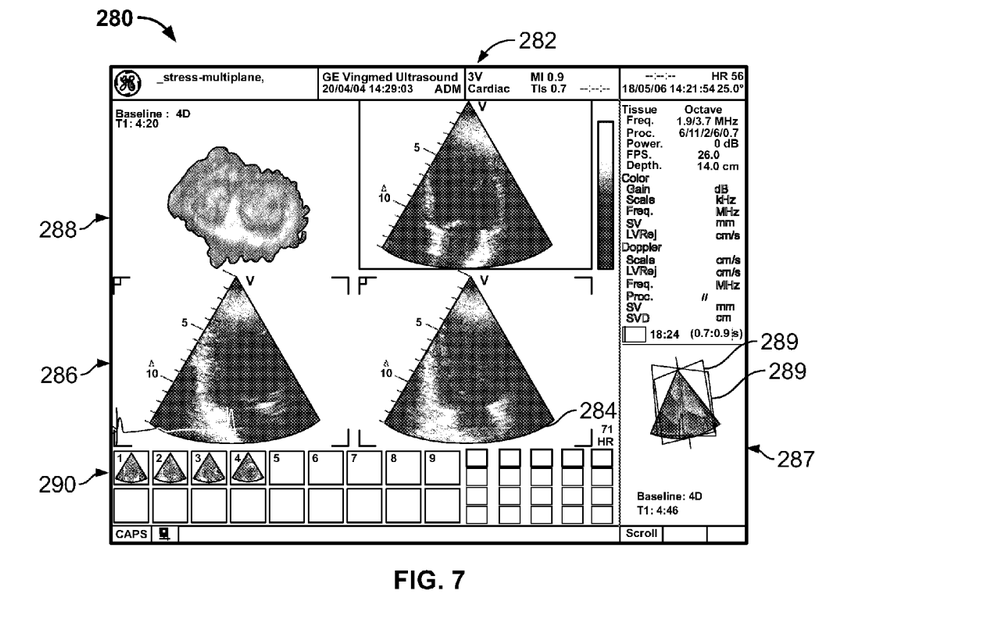
FIG. 7 is a display illustrating live 4D images displayed during acquisition in accordance with an embodiment of the invention.

Once the protocol template 200 is established, for example, by a user selecting the various parameters as described above, a protocol based ultrasound examination may be performed as illustrated in the method 250 of FIG. 6. Specifically, at 252, 4D acquisition and display is activated automatically according to a predefined protocol template, for example, as defined by the protocol template 200. For example, the protocol template 200 may be set up to acquire 4D images into one or more columns of a protocol template consisting of a multi-dimensional grid (as shown in FIG. 5). Thus, the activation includes setting up the acquisition and a screen layout where the user can acquire and see appropriate views of, for example, the 4D dataset during acquisition as shown in FIG. 7. The display 280 shown in FIG. 7 illustrates a single screen acquisition of three apical cut planes displayed in 4D that guides a user to acquire, for example, the whole left ventricle of the heart. In the illustrated embodiment, the display 280 is divided into quadrants with the quadrant 282 displaying a 4-chamber view, quadrant 284 displaying an apical long axis view (APLAX) and quadrant 286 displaying a 2-chamber view. Images for each of the quadrants 282-286 may be acquired for each stress level. Additionally, quadrant 288 may display a three-dimensional rendering. A plurality of image panes 290 also may be displayed (e.g., image thumbnails) that show the sequence of the acquired images. In addition to the rendered images shown in each of the quadrants 282-286, a geometric view 287 may be displayed showing the different cut planes 289.

It should be noted that the acquired views may be of different types, for example, cutplane views, rendering views, views based on automatically segmenting the image data or other views of the 4D dataset. For example, in the upper left pane or quadrant of the display, a short axis cutplane may be displayed instead of a volume rendering. Also, any number of images extracted from the 4D dataset may be displayed, for example, more or less than four images.

Acquisition and display setup information may be stored at 254 for later automatic retrieval. For example, the setup of the acquisition and display may be automatically stored so that this information may be reused at a later stage based on the position in the protocol. This may include parameters such as geometry of the scan, frequency, cutplane angles and other imaging and display parameters. For example, it may be appropriate to set up a similar acquisition and display when acquiring a 4D image on the next row 206 of the protocol in the same column 204 (both shown in FIG. 5). As another example, the settings may be reused in a later exam based on the same or a related protocol template 200. Additional or different information also may be stored at 254, for example, system parameters. For example, an elevation height for a portion of the examination table (e.g., front panel) on which a patient is being examined may be stored for each view in a protocol and, for example, the height of the frontpanel may be automatically adjusted for each stress level.

Figure 8:
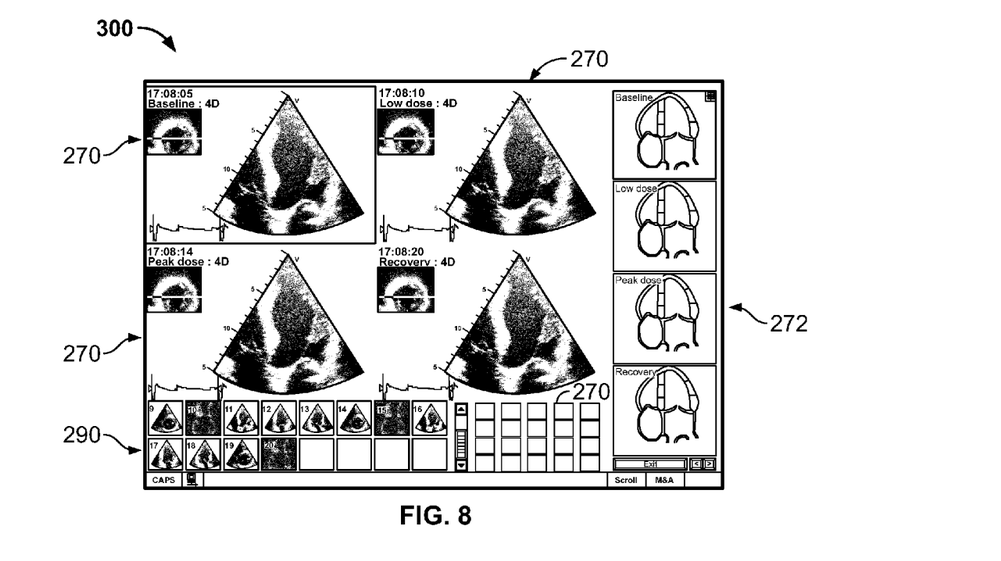
FIG. 8 is a display illustrating long-axis views of a heart (equivalent to apical views when scanned in 2D) at different stress levels in accordance with an embodiment of the invention.

During the ultrasound scan based on the protocol, image orientations at different stress levels, for example, the image orientations between images in a single column 204 on different rows 206 (both shown in FIG. 5) are maintained at 256. For example, the relative angle and rotation of the cut plane is maintained for a given view (e.g., 2-chamber view) throughout the various stress levels (which may be time-synchronized by ECG). Thus, as shown in FIG. 8, four apical views 270 at different stress levels (e.g., base level, low, peak and recovery) may be displayed at the same time with the same orientation. Additionally, wall motion scoring may be displayed in a scoring portion 272 wherein wall motion scoring is shown for each of the corresponding projections.

Figure 10:
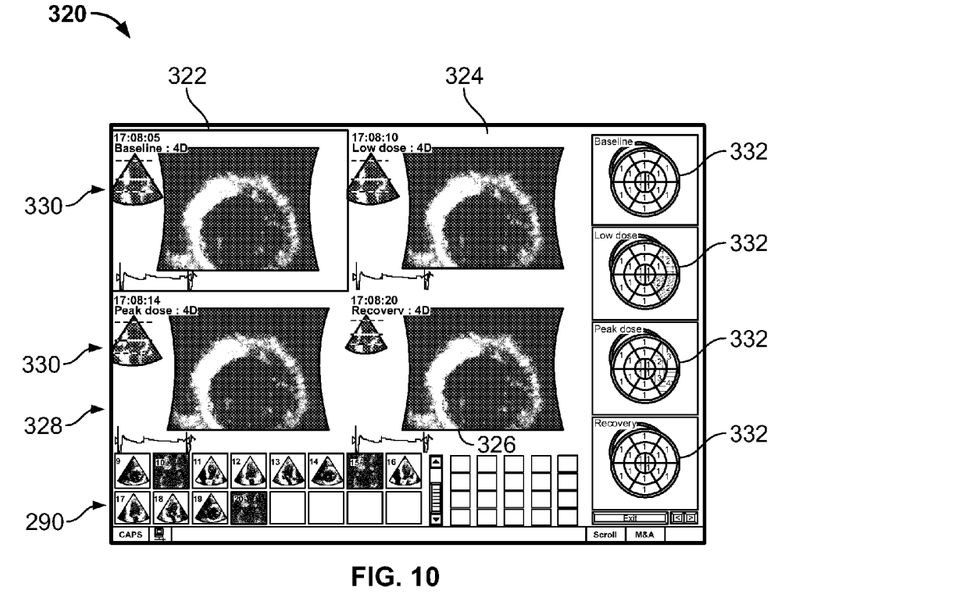
FIG. 10 is a display illustrating short-axis views of a heart (equivalent to parasternal views when scanned in 2D) at different stress levels in accordance with an embodiment of the invention.

As another example, the cut plane may be changed in multiple short axis view. For example, as shown in FIG. 10, a display 320 may simultaneously display a single short axis slice at four different stress levels (which may be time-synchronized by ECG) represented by the images in quadrants 322, 324, 326 and 328 of display 320. For example, all short axis cut planes of the left ventricle may be viewed simultaneously and modified synchronously. Additionally, a cut plane identifier 330 (in this embodiment illustrating the short axis slice by a colored line on a 4-chamber image) is provided in each quadrant 322, 324, 326 and 328. The cut plane identifier indicates the location of the cut plane for the image in the current quadrant (shown as a solid line). The cut plane line (solid line) can be translated up and down (along the main axis defined by the organ under investigation) in two ways including, jumping between the apex, mid and basal levels or translating the planes in smaller steps or increments between the limits defined by the top and bottom lines (shown as dotted lines). Additionally, the dotted upper and lower lines may be moved (e.g. by dragging with a user controller). The different images may be updated based on changes to one of the images (e.g., the current slice plane will translate synchronously in all volumes). Additionally, other indicators may be updated based on movement of the cut planes, for example, wall motion scoring displayed on bulls-eyes plots 332 (which may be displayed as is known).

Standard imaging planes also may be extracted from a 4D dataset at 258. In particular, after acquiring several 4D images into a protocol, several standard image projections from each image may be extracted. For example, in cardiology, typically the standard projections are the 4-chamber view, 2-chamber view, apical long axis view, short axis view from apex, mid and basal level of the heart. In a stress-echo examination, and as illustrated in FIG. 5, wherein the rows 206 in the protocol template 200 represent stress levels and the columns 204 represent projections or probe positions, standard image projections corresponding to each cell 202 may be extracted based on, for example, previous or currently acquired ultrasound scan datasets. Accordingly, using the extracted standard imaging planes, the resulting images in the protocol can be easier to analyze after the scan because the images correspond to typical views. Alignment of 4D datasets by rotation and translation after acquisition is thereby reduced as the 4D datasets will typically be aligned properly during the acquisition phase of the examination.

Automatic extraction of standard views may be provided, for example, in the following sequence defining default images:

"Apical analysis" in plane 1 (4-chamber/probe plane).

"Apical analysis" in plane 2 (2-chamber)–Angle1 (e.g., rotated −60 degrees from plane 1 around the main axis A). Angle1 may be defined during image acquisition by rotating the 2-ch projection in the live acquisition display.

"Apical analysis" in plane 3 (ApLAX)–Angle2 (e.g., rotated −120 degrees from plane 1 around the main axis A). Angle2 may be defined during image acquisition by rotating the APLAX projection in the live acquisition display.

"Short axis analysis" in apical plane level of the heart, in a plane perpendicular to the main axis A (17% or ⅙ along the distance from top toward bottom, for example, the middle of the apical myocardial segments of a 16, 17 or 18 segment model).

"Short axis analysis" in mid plane level of the heart, in a plane perpendicular to the main axis A (50% or ½ along the distance from top toward bottom, for example, the middle of mid myocardial segments at the level of papillary muscles).

"Short axis analysis" in basal plane level of the heart, in a plane perpendicular to the main axis A (83% or ⅚ along the distance from top toward bottom, for example, middle of the basal segments).

Thereafter, the next analysis group (as defined in template) is opened.

In this automatic extraction process, a main axis A is defined for extracting the images. In a cardiac application, the main axis A is aligned along the left ventricle main axis of the heart (mid longitudinal axis in the left ventricle of the heart). By default, the main axis is equivalent to the probe main axis. In instances where the probe main axis is tilted and not properly aligned during acquisition with the left ventricle main access, user adjustment may be provided. In a stress-echo application, a different main axis A is defined in each volume.

It should be noted that in the apical plane analysis (or long axis analysis) the image planes are displayed along the main axis A with rotation around that main axis allowed. The rotation is performed in all volumes simultaneously, for example, by a user rotating a single rotary control. It should be noted that in the short axis analysis the image planes are displayed perpendicular to the main axis A with translation allowed. The translation is performed in all volumes simultaneously, for example, by a user rotating a single rotary control. Top and bottom planes may be adjusted as described in more detail below using other rotary controls. This movement is individual to each 4D volume. In general, the top plane is typically placed at the top of the apical segments and the bottom plane is places at the bottom of the basal segments as defined above.

Figure 9:
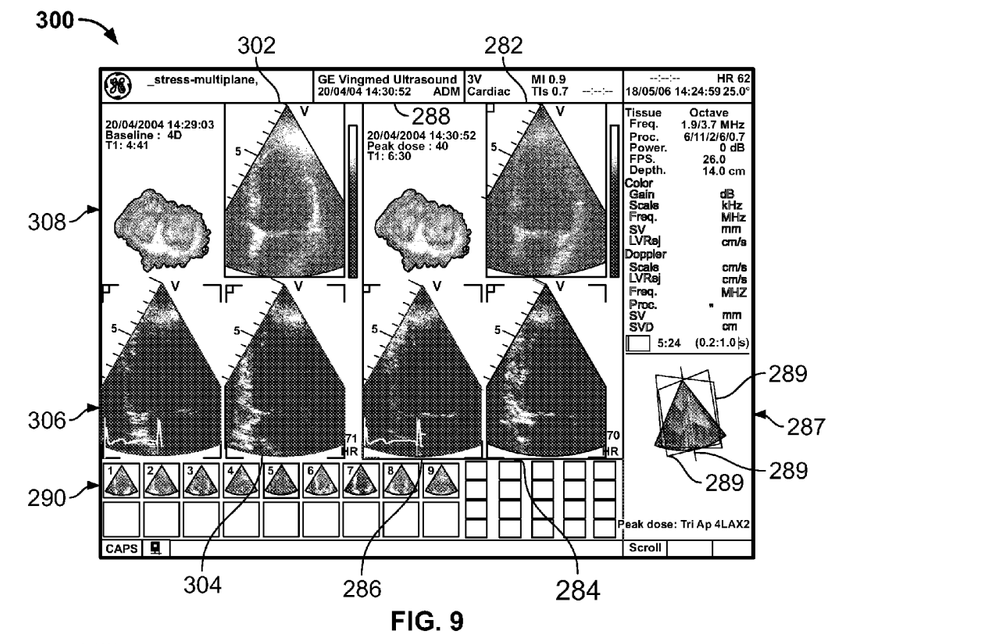
FIG. 9 is a display illustrating both live and reference 4D images displayed on a single screen in accordance with an embodiment of the invention.

Reference images also may be displayed during acquisition at 260 and as shown in the display 300 of FIG. 9. In the display 300, standard image projections are shown in quadrants 302, 304 and 306 (with quadrant 308 showing a three-dimensional rendering), which correspond to quadrants 282, 284, 286 and 288, respectively. This "show reference" functionality may be disabled or enabled before, after or during any portion of the ultrasound exam. In operation, when 4D images (or other images) are to be acquired into the protocol, one or more "reference images" together with the display from live acquisition are displayed. For example, as shown in FIG. 9, a side-by-side screen layout may be provided where one reference image is shown on left side and a live image is shown on the right side or vice versa. It should be noted that the reference image may be any image that may guide the user to acquire a correct or desired image. For example, the reference image may be an equally oriented image from a baseline row in the protocol or from previous rows in the protocol. The reference image also may be an image from a previous examination on the same patient, or the reference image may be a general guidance image illustrating the orientation or projections to be acquired. One or more reference images may be synchronized by live ECG signals.

Thus, a full volume acquisition with rotation of image planes may be acquired as follows:

Plane 1 (top view) shows "probe plane" (i.e. the view seen when scanning 2D with the 4D probe), and this view is geometrically fixed.

Planes 2 and 3 by default are rotated −60 and −120 degrees from probe plane (rotation axis=center long-axis of probe plane), which will result in approximately the 2-chamber and ApLAX views given that the probe plane is the 4-chamber view.

Planes 2 and 3 each have an associated rotary and trackball assignment, Angle1 and Angle2 respectively, which can be used to find the correct apical projection. Angle1 and Angle2 will be displayed on screen. Also, Angle1 and Angle2 may be stored to file such that these planes can be recalled during analysis.

Thus, in cases where related images are to show the same projection or orientation of the organ under investigation, a reference image mechanism and the storage of acquisition and display setup guides the user to acquire equal images.

A technical effect of at least one embodiment of the invention is the reduction of time to acquire images at different stress levels during a stress-echo protocol based examination by acquiring all projections for analysis during one or a few heart cycles. Image acquisition, particularly for 4D ultrasound protocol based examinations, may be based on automatically extracted standard imaging planes from a 4D dataset that may be used for analysis.

Exemplary embodiments of diagnostic ultrasound systems are described above in detail. The systems are not limited to the specific embodiments described herein, but rather, components of each system may be utilized independently and separately from other components described herein. Each system component can also be used in combination with other system components.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using graphics processing units (GPUs), microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

While the invention has been described in terms of various specific embodiments, those skilled in the art will recognize that the invention can be practiced with modification within the spirit and scope of the claims.

What is claimed is:

1. A method for acquiring four-dimensional (4D) ultrasound images of a heart in a protocol based examination, the method comprising:
   acquiring 4D ultrasound scan data during a protocol based examination;
   aligning images formed from the 4D ultrasound scan data while the 4D ultrasound scan data is being acquired; and
   displaying the aligned images with a reference image formed from previously-acquired 4D ultrasound scan data while the 4D ultrasound scan data is being acquired, wherein the aligned images and the reference image are acquired when the heart is at different stress levels and has different heart rates, the aligned images and the reference image being synchronized using electrocardiogram data and displayed simultaneously.

2. A method in accordance with claim 1 further comprising automatically extracting the plurality of standard image projections for each image.

3. A method in accordance with claim 2 wherein the standard image projections are based on a probe plane view that is geometrically fixed.

4. A method in accordance with claim 3 wherein the probe plane comprises a 4-chamber view.

5. A method in accordance with claim 3 wherein the standard image projections are based on additional planes rotated from a probe plane and further comprising storing angle information corresponding to each of the additional planes.

6. A method in accordance with claim 5 wherein the angle information defines apical projections that are automatically extracted.

7. A method in accordance with claim 2 wherein the automatic extraction is based on one of an apical plane analysis and a short axis analysis.

8. A method in accordance with claim 2 wherein the automatic extraction is based on at least one of the following:
   Apical analysis in plane 1 (4-chamber/probe plane);
   Apical analysis in plane 2 (2-chamber) based on a first angle;
   Apical analysis in plane 3 (Apical long axis) based on a second angle;
   Short axis analysis in apical plane (17% from top toward bottom);
   Short axis analysis in mid plane (50% from top toward bottom); and
   Short axis analysis in basal plane (83% from top toward bottom).

9. A method in accordance with claim 1 further comprising displaying at least three apical cut planes of the heart during acquisition.

10. A method in accordance with claim 1 further comprising displaying at least one rendering view and one geometric view corresponding to the images.

11. A method in accordance with claim 1 wherein the standard image projections are extracted based on a protocol template.

12. A method in accordance with claim 1 further comprising storing at least one of acquisition parameters, display parameters and system parameters that are accessible at a later time and based on a position in a protocol template.

13. A method in accordance with claim 1 wherein the standard image projections are based on one of an axis and coordinate system that is at least one of translated and rotated relative to one of a probe main axis and a probe coordinate system.

14. A method in accordance with claim 1 wherein the standard image projections comprise a 4-chamber view, a 2-chamber view, an apical long axis view, and a short axis view from each of an apex, mid and basal level of the heart.

15. A method in accordance with claim 1 wherein the protocol based examination comprises a stress-echo examination.

16. A method in accordance with claim 1 wherein acquiring 4D ultrasound scan data comprises acquiring data at a rate of at least twenty-five frames per second.

17. A method in accordance with claim 1 wherein acquiring 4D ultrasound scan data comprises acquiring data at a rate of at least thirty frames per second.

18. The method of claim 1, wherein the reference image includes a plurality of reference images corresponding to different standard imaging projections of the heart during a stress-echo examination, each one of the aligned images corresponding to one of the reference images that has a equal imaging projection, each of the reference images and the corresponding aligned image being synchronized using electrocardiogram data.

19. The method of claim 18, wherein each of the reference images is acquired at a first stress level and each of the aligned images is acquired during a different second stress level.

20. The method of claim 1, wherein said acquiring 4D ultrasound scan data includes using an ultrasound probe, the probe receiving a plurality of beams using multi-line acquisition.

21. An ultrasound system comprising:
- a probe configured to acquire ultrasound volume data of a heart for a protocol based examination;
- a processor configured to process aligned four-dimensional (4D) images formed from the ultrasound volume data while the ultrasound volume data is being acquired to automatically extract standard image projections; and
- a display for displaying the aligned images with a reference image formed from previously-acquired 4D ultrasound scan data while the ultrasound volume data is being acquired, wherein the aligned images and the reference image are acquired when the heart is at different stress levels and has different heart rates, the aligned images and the reference image being synchronized using electrocardiogram data and displayed simultaneously.

22. An ultrasound system in accordance with claim 21 wherein the probe is configured to acquire the ultrasound volume data at a rate of at least 25 frames per second.

* * * * *